(12) United States Patent
Cerutti

(10) Patent No.: US 8,528,421 B2
(45) Date of Patent: Sep. 10, 2013

(54) DEVICE FOR MEASURING THE TORQUE OF A HAIRSPRING

(75) Inventor: Marc Cerutti, Saint-Julien-en-Genevois (FR)

(73) Assignee: Rolex S.A., Geneva (CH)

( * ) Notice: Subject to any disclaimer, the term of this patent is extended or adjusted under 35 U.S.C. 154(b) by 224 days.

(21) Appl. No.: 13/219,212

(22) Filed: Aug. 26, 2011

(65) Prior Publication Data

US 2012/0048035 A1    Mar. 1, 2012

(30) Foreign Application Priority Data

Aug. 31, 2010   (EP) ..................................... 10405156

(51) Int. Cl.
*G01L 3/02*           (2006.01)

(52) U.S. Cl.
USPC .................................. 73/862.321; 73/862.08

(58) Field of Classification Search
USPC ....................................... 73/862.08, 862.321
See application file for complete search history.

(56) References Cited

U.S. PATENT DOCUMENTS

| | | | | |
|---|---|---|---|---|
| 3,927,559 A | * | 12/1975 | Da Costa et al. | 73/862.08 |
| 6,863,435 B2 | * | 3/2005 | Moteki et al. | 368/140 |
| 8,393,783 B2 | * | 3/2013 | Daout et al. | 368/175 |
| 2013/0064046 A1 | * | 3/2013 | Rochat | 368/177 |

FOREIGN PATENT DOCUMENTS

| | | |
|---|---|---|
| CH | 372610 A | 6/1963 |
| DE | 1523801 A1 | 7/1969 |

OTHER PUBLICATIONS

European Search Report of EP 10405156, date of mailing Feb. 8, 2011.

* cited by examiner

*Primary Examiner* — Max Noori
(74) *Attorney, Agent, or Firm* — Westerman, Hattori, Daniels & Adrian, LLP

(57) ABSTRACT

A device for measuring the torque of a hairspring for a balance wheel-hairspring oscillator includes an arbor on which a seat is arranged, a benchmark element, pivoting means for pivoting the arbor, means for keeping the outer end of the hairspring fixed relative to the arbor during measurement, elastic elements provided on a portion of the seat, and means for acting on the elastic elements. The inner end of said hairspring is secured to a collet, the diameter of the seat of the arbor is of a dimension to allow a driving connection by friction with the wall of an axial aperture of the collet, and the elastic elements are formed to bring, under the action of the action means, the section of the portion of the seat forming the driving connection from a greater dimension to a smaller dimension than that of the axial aperture of the collet.

16 Claims, 2 Drawing Sheets

DEVICE FOR MEASURING THE TORQUE OF A HAIRSPRING

The present invention relates to a device for measuring the torque of a hairspring for a balance wheel-hairspring oscillator, comprising an arbor, a benchmark element, such as a hairspring or a flywheel, associated with said arbor, pivoting means for pivoting said arbor, a seat arranged on this arbor, the diameter of which is of a dimension to allow a driving connection by friction with the wall of an axial aperture of a collet secured to the inner end of said hairspring and means for keeping the outer end of said hairspring fixed relative to said arbor during the measurement.

The inaccuracies and geometric dispersions of the method for manufacturing a hairspring, although slight, nevertheless cause a dispersion of the torque of the hairsprings relative to a target value of typically 1%. This is observed both on the hairsprings of Archimedes spiral type made from metal alloy wires such as the Invar®, Elinvar® or Parachrom® alloys, and on the hairsprings obtained by micromanufacturing methods from silicon, diamond or quartz wafers.

The operating precision required of a balance wheel-hairspring oscillator is of the order of a few seconds per day, which represents a precision of a few tens of ppm. The oscillation frequency of balance wheel-hairspring oscillators may be adjusted by various means, such as for example by nuts or weights the position of which relative to the balance wheel rim is adjustable, which modifies the inertia of the balance wheel. The range of adjustment is typically 100 s/d, which is insufficient to obtain precise operation by arbitrarily linking a balance wheel with a hairspring.

For this reason, it is necessary to measure the characteristics of the hairspring and/or of the balance wheel before linking them, using a method that is known as pairing or matching. As explained below, the pairing methods known in the prior art are unsatisfactory, in particular for hairsprings made of a material that exhibits no range of plastic deformation, such as silicon for example.

The specific frequency f of the mechanical oscillating system of a watch consisting of a hairspring and a balance wheel is $f=(1/2\pi)\sqrt{(C/I)}$, where C is the torque of the hairspring and I the moment of inertia of the whole oscillating system (as a first approximation equal to the moment of inertia of the balance wheel). The balance wheel and the hairspring may be calibrated so that the specific frequency sought is obtained with a precision of at least two to five minutes per day, therefore of an order of magnitude of 1‰. The fine tuning is then carried out on the watch, for example with the aid of a regulator or of means for adjusting the inertia of an inertia-adjustable balance wheel by means of nuts, screws or weights, that can be moved along a radial axis relative to the flywheel which is formed by the balance wheel.

According to the "Théorie d'horlogerie" ("Theory of clockmaking") (Reymondin et al., Simonin 1998), there are three methods of pairing a hairspring with a balance wheel to form a balance wheel-hairspring oscillator of given frequency:

a comparative measurement of operation of the balance wheel-hairspring oscillator relative to a benchmark balance wheel-hairspring, with comparison by beat or phase shift, and adjustment of the inertia of the balance wheel and/or of the active length of the hairspring;
  a comparison of the frequency of the balance wheel-hairspring oscillator with a high-precision oscillator such as a quartz, and adjustment as above;
  the sorting of a set of hairsprings and of balance wheels into classes, with pairing of a hairspring and of a balance wheel of corresponding classes to obtain a balance wheel-hairspring oscillator of given frequency with a maximum difference of ±2 minutes/day compared with the target frequency.

There are two measurement methods, the static method which consists in measuring the torque of the hairspring, as described in U.S. Pat. No. 2,384,520 or in EP 2 128 723 and the dynamic method, described notably by FR 1 502 464 or in CH 690 874.

These measurements may be used either to adjust the frequency by modifying the inertia of the balance wheel by removing material with the aid of a milling machine (CH 690 874) or of a laser (CH 609 196) or by adjusting the length of the hairspring as in FR 1 502 464, or to divide the hairsprings and the balance wheels into classes as a function of the torque of the hairsprings and the inertia of the balance wheels, as described notably by P.-L. Gagnebin in the instruments of the Congrès Suisse de Chronométrie (Swiss Chronometry Congress) 1966, p. 321.

This procedure consists in dividing the balance wheels and hairsprings into classes by comparative measurement with a benchmark, and in linking a balance wheel with a hairspring of corresponding class. One option for measuring the torque of a hairspring consists in fixing its inner end to a collet that is chased onto an arbor associated with a flywheel (balance wheel) of determined inertia, and in measuring the resultant frequency of this oscillator, which makes it possible to determine the torque of the hairspring by dynamic measurement, the inertia of the balance wheel being known. After this measurement operation, the hairspring must be detached from the benchmark balance wheel.

It is also possible to carry out a static measurement by comparing the torque of the hairspring to be tested with that of a benchmark hairspring, as in U.S. Pat. No. 2,384,520 or in EP 2 128 723 above-mentioned.

The German patent application published under number DE 15 23 801 relates to a metering device with an elastic element on the arbor, designed to operate with a hairspring with no collet. This system (called below the "Kiesewetter system" from the name of its inventor) is designed for hairsprings the end of which is directly fixed to the spindle and it operates only in a very particular case: it aims to allow the metering of a hairspring with no collet, directly attached to the balance wheel arbor. It cannot be used with a standard balance wheel arbor. Moreover, attaching a hairspring directly to the arbor is not without its problems, which is why this system has not found a practical use in clockmaking. Specifically, this attachment is carried out by welding. However, this welding of the end of the hairspring directly to the arbor must be carried out under perfect control so that the hairspring is centered and flat. The welding must be mechanically robust, which is far from being guaranteed for such a configuration. Moreover, the hairspring cannot be removed, which is prohibitive because it is then necessary to change the whole balance wheel-hairspring if there is a problem. For example, if the pivots are damaged following an impact, it is necessary to change the assembly instead of changing only the arbor after removing the various elements, which involves a considerable extra cost.

The Kiesewetter system therefore operates only with hairsprings that are directly attached to the spindle and it cannot be directly transposed to a hairspring comprising a collet, because no element on the collet is provided to allow securing to the spindle by pinching. If such an element were to be added to the collet, the arbor of the balance wheel intended to produce the balance wheel-hairspring oscillator would also have to be modified.

Moreover, this principle is difficult to apply on a hairspring made of fragile material such as Si, because the pinching/clamping risks damaging the blade and the inner end of the hairspring should then be fixed to the arbor of the balance wheel in order to form the balance wheel-hairspring oscillator. The only known method of assembly for the hairsprings is then bonding (securing the outer end to the stud).

The arbor used in the Kiesewetter system is an assembly of at least three parts: the arbor itself with the balance wheel, the spring 8 and the clamping cone 7, which are moved each time a hairspring is secured to the arbor. This can cause balancing defects (movement of the center of gravity relative to the pivoting axis) which interfere with the measurement.

Moreover, in the case of hairsprings made of a material with no range of elastic deformation, such as silicon, the collet is usually made in one piece with the hairspring, so that the chasing and removing of the hairspring carries a high risk of breakage, in particular at the collet.

The object of the present invention is notably to obviate the many drawbacks of the aforementioned Kiesewetter system and to at least partly remedy the abovementioned risk of breakage.

Accordingly, the subject of this invention is a device for the measurement of the torque of a hairspring for a balance wheel-hairspring oscillator according to Claim 1.

Preferably, this device is used for the dynamic measurement of the torque of a hairspring for a balance wheel-hairspring oscillator, in which said arbor is secured to a flywheel of determined inertia.

This invention is particularly useful when the hairspring to be measured is a hairspring made of a material with no range of elastic deformation, such as silicon, diamond or quartz.

The manufacture of silicon hairsprings, for which the present invention is more particularly, but not exclusively, intended, uses the same photolithography technique as for the manufacture of microelectronics components. A resin mask is formed on the surface of a silicon wafer and defines the geometry of the components. A deep etching is then used to remove material in the places that are not protected by the mask and thus to produce the components, either on a single level (identical geometry over the whole thickness of the component), or on several levels. A thermal oxidation is then carried out in order to cover the silicon with a layer of silicon oxide in order to obtain a resultant thermal coefficient of the hairspring such that the linking of this hairspring with a normal monometallic balance wheel makes it possible to produce a thermocompensated balance wheel-hairspring oscillator, that is to say an oscillator exhibiting little or no variation in operation with the temperature, as described in EP1422436. The hairspring is then metered and classed.

Checking the torque of each hairspring, preferably carried out by measuring its oscillation frequency once the latter is linked to a benchmark balance wheel, can advantageously be carried out while the hairsprings are still secured to the silicon wafer, secured to a fixed point relative to the oscillation arbor of the measurement device, or also once the hairsprings have been detached from the wafer.

The ideal situation is to be able to carry out the measurement, static or preferably dynamic measurement, by measuring the frequency while the hairspring is still attached to the silicon wafer in which it has been etched. However, this poses constraints with respect to the means used for taking the measurement. To take this measurement on a wafer of typically 150 mm diameter (6" wafer), it would be advantageous, for reasons of simplicity of application, for the mechanical measurement means to be on one and the same side of the wafer.

The appended drawings illustrate, schematically and as an example, one embodiment of the measurement device that is the subject of the present invention.

Figure 1:
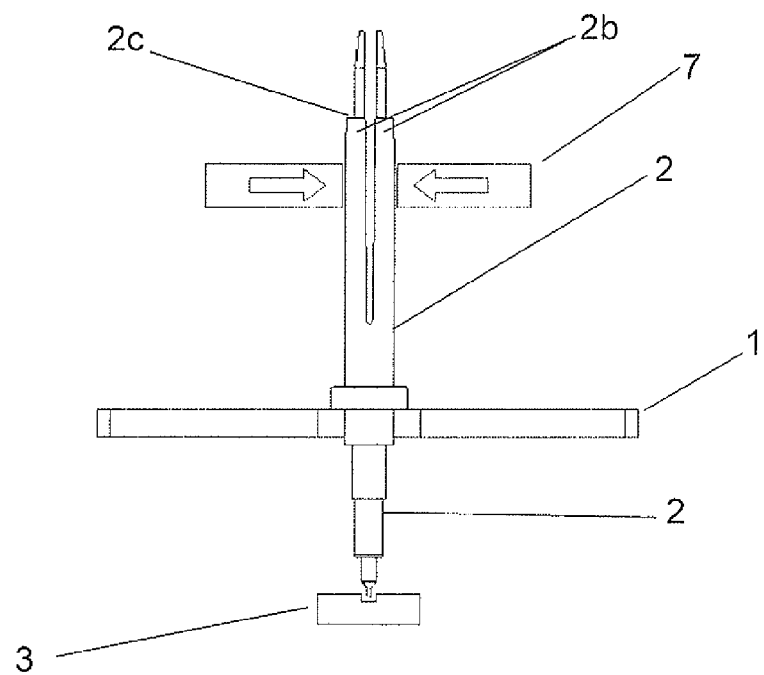
FIG. 1 is a view in elevation and in section of this device.
Figure 2:
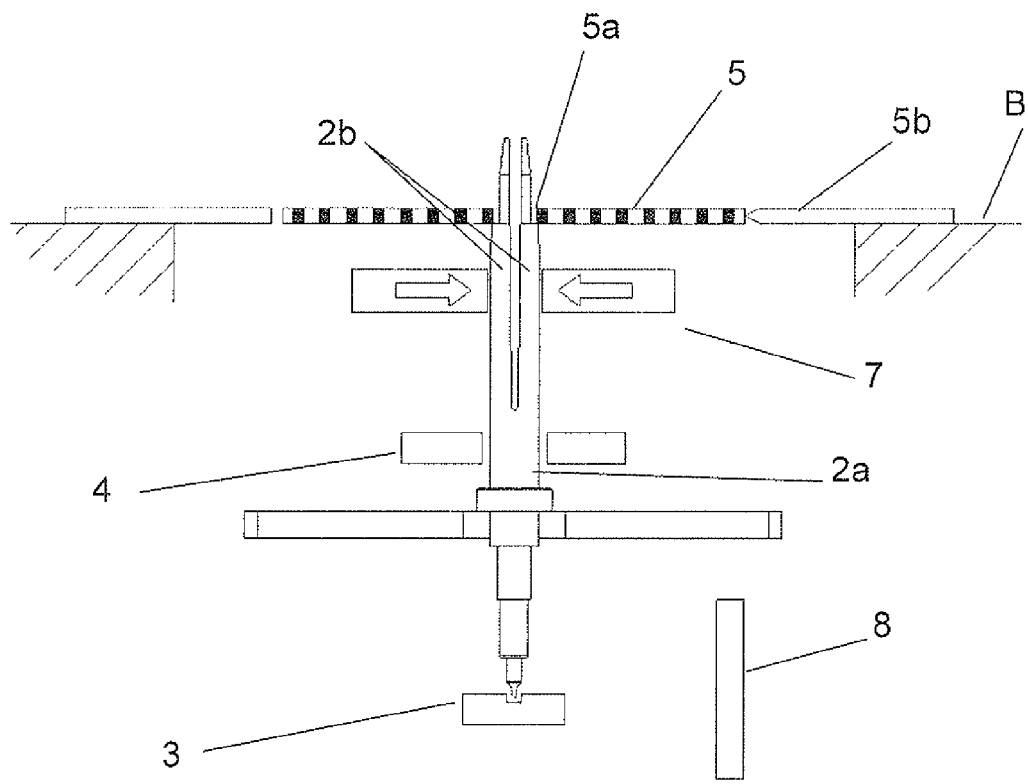
FIG. 2 is a view similar to that of FIG. 1 showing this device with a hairspring mounted on it.

The measurement device according to the invention preferably comprises a benchmark balance wheel comprising a flywheel 1 of determined inertia mounted on an arbor 2 the bottom end of which rests in a pivoting bearing 3. This device is designed for the dynamic measurement of the torque of the hairspring. According to a variant not shown, instead of a flywheel 1, the arbor 2 could be linked with a benchmark hairspring, of determined torque, which would make it possible to take a static measurement, that is less precise, of the torque.

A second pivoting 4 can be provided by an air bearing placed just above the flywheel 1 for example. The second pivoting can also be provided only by the hairspring 5 still attached to the silicon wafer 5b in which it has been etched and fixed to a frame B on which the measurement device is mounted. This variant reduces the quality factor, but the tests show that the precision obtained during the frequency measurement remains sufficient to carry out a pairing.

The hairspring 5 is preferably etched in a silicon wafer 5b with a collet 5a made in one piece with its internal end and furnished with an axial aperture in order to engage with the upper portion 2a of the arbor 2 which serves as a seat.

Figure 3:
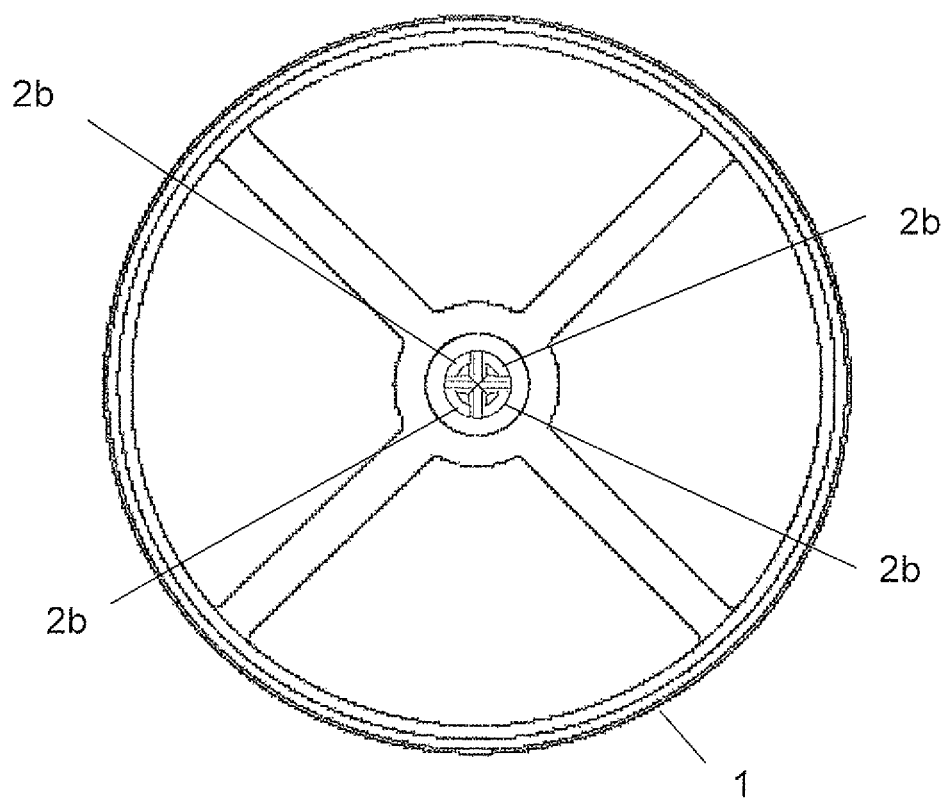
FIG. 3 is a view from the top of FIG. 1.

The portion 2a of the arbor 2 situated above the flywheel 1 is split diametrally, thus arranging elastic elements 2b. Advantageously, two diametral splits forming between them an angle of 90° are arranged as illustrated in FIG. 3. The elastic elements 2b are linked with a clamping pincer 7. The latter makes it possible to alter the section of the upper portion 2a of the arbor 2 from a greater dimension to a smaller dimension than that of the axial aperture of said collet 5a, which makes it possible not to mechanically stress the collet and the hairspring when the hairspring is attached to and separated from the portion 2a of the arbor 2 and thus to prevent breakages due to the weakness of the silicon.

The oscillation frequency of the measurement device described above may advantageously be measured in a known manner by optical means 8. Since measurement of the frequency does not form part of the invention, it will not be described because it is not necessary to the comprehension of the invention.

Advantageously, the seat of the upper portion 2a of the arbor 2 designed to receive the collet 5a of the hairspring 5 comprises a bearing surface 2c to allow a precise positioning of the hairspring 5 along the arbor 2. Preferably, the upper portion 2a of the latter has a conical portion at its upper end in order to make it easier to engage the axial aperture of the collet 5a.

Compared with the Kiesewetter system, this system is therefore much more simple, the arbor comprising fewer elements. Working spread out to secure the collet to the arbor makes it possible to advantageously replace the fitted and moving elements (spring and cone) of the Kiesewetter system with elastic elements arranged on the arbor, which do not change the balancing of the balance wheel.

Moreover, the reversal of the steps of reducing and enlarging the diameter has several important consequences. Specifically, enlarging the diameter of the arbor to secure the collet-hairspring assembly to the device makes it possible to:

remove the fitted and movable parts on the arbor of the Kiesewetter system which introduce additional and uncontrolled balancing defects, the latter being able to vary from one measurement and from one hairspring to another;

secure a hairspring fitted with a collet to the arbor, which is not possible with the Kiesewetter system;

drive the hairspring and its collet by friction only, instead of a mechanical movement in the case of the Kiesewetter system, which involves a mechanical stress and strains that are not negligible.

In one exemplary embodiment, the clamping pincer 7 makes it possible to reduce the diameter of the arbor by more than 30% at its end. For example, the diameter of the axial aperture of the collet is 0.5 mm and the external diameter of the split arbor of the checking device is 0.6 mm. The clamping pincer 7 makes it possible to reduce this diameter to 0.4 mm and allows the portion 2a of the arbor 2 to be inserted through the axial aperture of the collet 5a with no friction. Since the forces produced by the elastic elements 2b when the clamping pincer 7 is relaxed are purely radial, the risk of breakage of the collet 5a is extremely low. The connection by friction of the collet 5a of the hairspring 5 after relaxing of the clamping pincer 7 is greater by several orders of magnitude than the friction force necessary to allow the measurement.

A typical sequence for measuring the torque of a hairspring with the aid of the device described may proceed in the following manner:

the measurement device is placed under the hairspring 5 to be measured;
the diameter of the portion 2a of the shaft 2 is reduced by the clamping pincer 7;
the portion 2a of the arbor 2 is inserted through the axial aperture of the collet 5a;
the clamping pincer 7 is relaxed;
the arbor 2 is released from the benchmark flywheel 1;
the arbor-flywheel-hairspring assembly is made to oscillate;
the frequency is measured;
the arbor 2 is stopped;
the diameter of the portion 2a of the arbor 2 is reduced by the clamping pincer 7;
the arbor 2 is withdrawn from the collet 5a;
the measurement device is moved to the next hairspring 5 etched in the silicon wafer 5b, so as to be able to take the next measurement.

Certain steps can naturally be carried out simultaneously.

The measurement device can be advantageously moved by a robot with 3 linear degrees of freedom (3DDL). To give an example, the hairsprings on the silicon wafer 5b are 10 mm apart, and the external diameter of the hairsprings 5 is 8 mm. The device makes it possible to measure the torque of all the hairsprings made on one and the same wafer (typically 175 hairsprings made on a wafer that is 150 mm in diameter).

Advantageously, the hairspring 5 is naturally held by the external attachment that links it to the wafer 5b. This makes it possible to keep its recess point fixed. If the hairspring is detached from the wafer 5b for the measurement, a means for immobilizing the attachment point of the outer end of the hairspring must be provided.

The invention claimed is:

1. Device for the dynamic or static measurement of the torque of a hairspring for a balance wheel-hairspring oscillator, comprising:
an arbor on which a seat is arranged,
a benchmark element, benchmark flywheel or hairspring, associated with said arbor,
pivoting means for pivoting said arbor,
means for keeping the outer end of said hairspring fixed relative to said arbor during the measurement,
elastic elements provided on a portion of said seat, and
means for acting on said elastic elements,
wherein the inner end of said hairspring is secured to a collet, the diameter of the seat of the arbor is of a dimension to allow a driving connection by friction with the wall of an axial aperture of the collet, and the elastic elements are formed to bring, under the action of the action means, the section of the portion of the seat forming the driving connection from a greater dimension to a smaller dimension than that of the axial aperture of the collet.

2. Device according to claim 1, in which the seat is formed in a portion of said arbor comprising at least one diametral slot in order to form said elastic elements.

3. Device according to claim 1, in which the seat is formed in a portion of said arbor the section of which reduces between this seat and the end of said arbor providing access to the seat.

4. Device according to claim 1, in which the pivoting axis of said arbor is vertical, said pivoting means comprising a bearing in which the bottom end of said arbor is engaged.

5. Device according to claim 4, in which said pivoting means comprise a second bearing.

6. Device according to claim 5, in which the second bearing is an air bearing.

7. Device according to claim 1, in which said means for acting on said elastic elements in order to bring the section of said seat to its smaller dimension than that of the axial aperture of said collet comprise a clamping pincer.

8. Device according to claim 1, in which said collet was made integral with said hairspring.

9. Device according to claim 1, in which said hairspring is made of one of the following materials: silicon, silicon with silicon oxide coating, quartz, diamond.

10. Device according to claim 1, in which, during the measurement, the outer end of the hairspring is secured to a wafer of said material in which said hairspring has been etched, this wafer being fixed to a frame.

11. Method for measuring the torque of a hairspring with the aid of a device according to claim 1, comprising the following steps:
the measurement device is placed under the hairspring to be measured;
the diameter of the portion of the shaft is reduced by the action of the action means;
the portion of the arbor is inserted through the axial aperture of the collet;
the action of the action means is relaxed;
the arbor is released from the benchmark flywheel;
the arbor-flywheel-hairspring assembly is made to oscillate;
the frequency is measured;
the arbor is stopped;
the diameter of the portion of the arbor is reduced by the action of the action means; and
the arbor is withdrawn from the collet.

12. Method for measuring the torque of a hairspring according to claim 11, in which the outer end of the hairspring is secured to a wafer made of the material in which this hairspring has been etched, this wafer being fixed to a frame.

13. Method for measuring the torque of a hairspring according to claim 11, in which the wafer comprises several hairsprings.

14. Method for measuring the torque of a hairspring according to claim 13, in which, once the arbor is withdrawn from the collet, the measurement device is moved to the next hairspring etched out of the silicon wafer.

15. Method for measuring the torque of a hairspring according to claim 11, also comprising a prior step of determining the inertia of the flywheel.

16. Method for measuring the torque of a hairspring according to claim 11, this method being applied by a robot.

* * * * *